US012616768B2

(12) United States Patent
Kendrick

(10) Patent No.: US 12,616,768 B2
(45) Date of Patent: May 5, 2026

(54) ENDOSCOPE DECONTAMINATION RACK

(71) Applicant: ASP GLOBAL MANUFACTURING GMBH, Schaffhausen (CH)

(72) Inventor: Alan Jefferson Kendrick, Laguna Beach, CA (US)

(73) Assignee: ASP Global Manufacturing GmbH, Schaffhausen (CH)

( * ) Notice: Subject to any disclaimer, the term of this patent is extended or adjusted under 35 U.S.C. 154(b) by 969 days.

(21) Appl. No.: 17/775,804

(22) PCT Filed: Nov. 24, 2020

(86) PCT No.: PCT/IB2020/061058
§ 371 (c)(1),
(2) Date: May 10, 2022

(87) PCT Pub. No.: WO2021/116805
PCT Pub. Date: Jun. 17, 2021

(65) Prior Publication Data
US 2022/0387651 A1     Dec. 8, 2022

Related U.S. Application Data

(60) Provisional application No. 62/948,168, filed on Dec. 13, 2019.

(51) Int. Cl.
*A61L 2/26* (2006.01)
*A61L 2/18* (2006.01)

(52) U.S. Cl.
CPC .................. *A61L 2/26* (2013.01); *A61L 2/18* (2013.01); *A61L 2202/15* (2013.01); *A61L 2202/24* (2013.01)

(58) Field of Classification Search
CPC ... A61B 50/33; A61L 2/18; A61L 2/26; A61L 2202/15; A61L 2202/182; A61L 2202/24
See application file for complete search history.

(56) References Cited

U.S. PATENT DOCUMENTS 6,555,054 B1 *    4/2003    Kral ........................ B08B 13/00
                                                   134/198
7,754,166 B2 *    7/2010    Jonsson .................... A61L 2/18
                                                   137/516.27
(Continued)

FOREIGN PATENT DOCUMENTS

CN          108607834 A    * 10/2018    ............... A61L 2/18

OTHER PUBLICATIONS

Chad Terhune, "Superbug outbreak: UCLA will test new scope-cleaning machine," LA Times, Jul. 22, 2015, http://www.latimes.com/business/la-fi-ucla-superbug-scope-testing-20150722-story.html, pp. 1-4.

*Primary Examiner* — Jennifer Wecker
*Assistant Examiner* — Brady C Pilsbury
(74) *Attorney, Agent, or Firm* — Lerner David LLP

(57) ABSTRACT

A decontamination rack is particularly suitable for decontaminating medical devices, such as endoscopes, for being designed to minimize shadowed surface area. The decontamination rack may be provided with internal channels through which a decontamination fluid may be supplied to the locations where a device contacts decontamination rack. These locations may comprise receiving areas having ejection ports with flexible nozzles disposed therein. The device may be disposed atop the nozzles such that the decontamination fluid exits the nozzles to impinge directly on those portions of the device that rest upon the nozzles. The use of the decontamination rack promotes improved or complete coverage of exposed external surfaces of the device with the decontamination fluid because decontamination fluid may be ejected into the receiving area to lift the device at the shadowed surface.

18 Claims, 4 Drawing Sheets

(56) References Cited

U.S. PATENT DOCUMENTS

| | | |
|---|---|---|
| 2002/0001537 A1 | 1/2002 | Hlebovy et al. |
| 2005/0025686 A1 | 2/2005 | Sargent et al. |
| 2015/0239018 A1 | 8/2015 | Voyer et al. |
| 2016/0242868 A1* | 8/2016 | Robert .................. A61B 50/22 |
| 2020/0214548 A1* | 7/2020 | Larsson ................. A61B 50/33 |

* cited by examiner

ENDOSCOPE DECONTAMINATION RACK

CROSS-REFERENCE TO RELATED APPLICATIONS

The present application is a U.S. National Phase Application of International Application No. PCT/IB2020/061058, filed Nov. 24, 2020, which claims priority to U.S. Provisional Patent Application No. 62/948,168, filed Dec. 13, 2019. The entire contents of these applications are incorporated by reference herein in their entirety.

FIELD

The subject matter disclosed herein relates to decontamination systems, particularly decontamination systems for decontaminating medical instruments.

BACKGROUND

Endoscopes are reusable medical devices. An endoscope should be reprocessed, i.e., cleaned and decontaminated, between medical procedures in which it is used to avoid causing infection or illness in a subject. Endoscopes are difficult to decontaminate as has been documented in various news stories. See, e.g., Chad Terhune, "Superbug outbreak: UCLA will test new scope-cleaning machine," LA Times, Jul. 22, 2015, http://www.latimes.com/business/la-fi-ucla-superbug-scope-testing-20150722-story.html (last visited Oct. 30, 2017).

One difficulty for reprocessing an endoscope arises when an endoscope must be coiled to fit into a decontamination system. Those portions of the endoscope that touch other portions of the endoscope or other materials within the sterilization chamber (e.g., a sterilization tray in which it is placed, a wall of the chamber, impermeable portions of a sterilization pouch) may be referred to as "shadowed surfaces." Shadowed surfaces are difficult to clean and decontaminate relative to exposed, i.e., non-shadowed, surfaces because it is more difficult to contact the shadowed surfaces with cleaning and disinfectant solutions.

SUMMARY OF THE DISCLOSURE

A decontamination rack may be used to decontaminate (e.g., sterilize or disinfect) medical devices, including those that have channels or lumens formed therethrough, such as endoscopes. The decontamination rack may fit a particular reprocessing tray design or universal processing trays. The decontamination rack may be designed to allow a tubular medical device, such as an endoscope, to be laid out such that shadowing may be minimized once the endoscope is disposed in the rack. The decontamination rack may be provided with internal channels through which a decontamination fluid may be supplied to the locations where the device contacts decontamination rack. These locations may comprise receiving areas having ejection ports with flexible nozzles disposed therein. The device may be disposed atop the nozzles such that the decontamination fluid exits the nozzles to impinge directly on those portions of the device that rest upon the nozzles. The use of the decontamination rack promotes improved or complete coverage of exposed external surfaces of the device with the decontamination fluid.

The decontamination rack may include a central portion and a first extension portion extending from the central portion. The first extension portion may comprise a receiving area, including a fluid ejection port located in the receiving area and a fluid pathway that fluidly connects a fluid inlet to the fluid ejection port. The fluid inlet may be a feature of the central portion.

The decontamination rack may be incorporated into a tray of a decontamination system. The fluid inlet may be connected to a source of decontamination fluid provided by the system.

A method of decontaminating the device includes disposing the device in a decontamination rack such that the instrument rests on at least one receiving area; and ejecting a decontamination fluid through a fluid ejection port of the receiving area such that the decontamination fluid contacts the instrument. The fluid may be ejected from the ejection port with sufficient force to lift the device off of the receiving area.

BRIEF DESCRIPTION OF THE DRAWINGS

While the specification concludes with claims, which particularly point out and distinctly claim the subject matter described herein, it is believed the subject matter will be better understood from the following description of certain examples taken in conjunction with the accompanying drawings, in which like reference numerals identify the same elements and in which:

MODES OF CARRYING OUT THE INVENTION

The following detailed description should be read with reference to the drawings, in which like elements in different drawings are identically numbered. The drawings, which are not necessarily to scale, depict selected embodiments and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

As used herein, the terms "about" or "approximately" for any numerical values or ranges indicate a suitable dimensional tolerance that allows the part or collection of components to function for its intended purpose as described herein. More specifically, "about" or "approximately" may refer to the range of values ±10% of the recited value, e.g. "about 90%" may refer to the range of values from 81% to 99%. In addition, as used herein, the terms "patient," "host," "user," and "subject" refer to any human or animal subject and are not intended to limit the systems or methods to human use, although use of the subject invention in a human patient represents a preferred embodiment.

Figure 1:
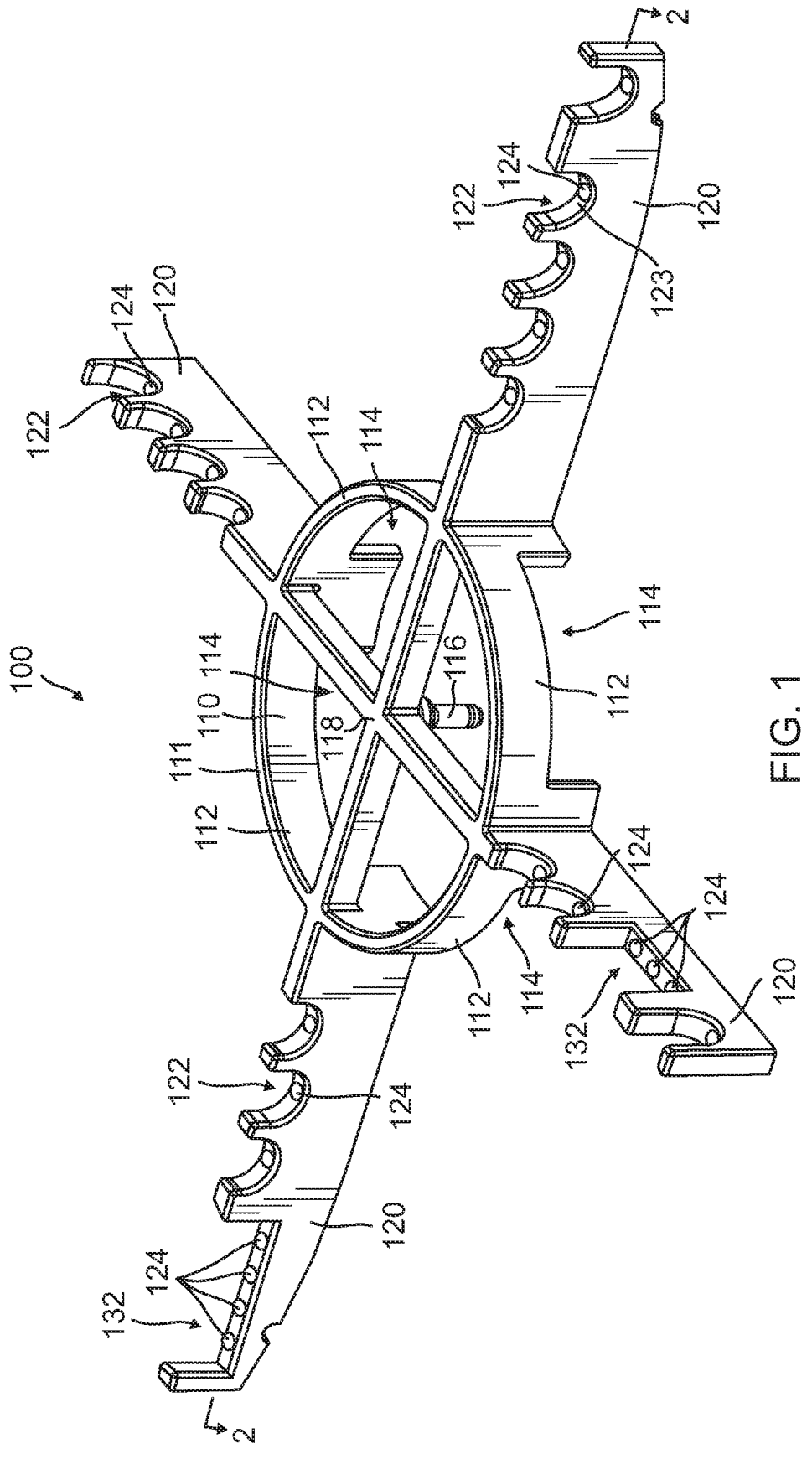
FIG. 1 depicts a perspective view of an exemplary decontamination rack.

FIG. 1 shows an exemplary decontamination rack 100 that is used to decontaminate (e.g., sterilize or disinfect) endoscopes and other medical devices that include channels or lumens formed therethrough. In FIG. 1, rack 100 fits a particular reprocessing tray design (FIG. 3). Rack 100 can fit other processing tray designs and/or universal processing trays. Rack 100 is designed to support an endoscope disposed therein out such that shadowing will be minimized. In addition, rack 100 has internal channels (for example, fluid pathway 140 in FIG. 2) that supply decontamination fluid (or other fluid) to the individual points where the endoscope sits in receiving areas 122, 132 of rack 100. The endoscope sits on nozzles (for example, fluid nozzles 150 in FIG. 2) mounted in receiving areas 122, 132 that feed the decontamination fluid to the bottom side of the endoscope at the points where the endoscope contacts rack 100. These nozzles may be flexible nozzles. The use of rack 100 promotes improved or complete coverage of the external surfaces of the endoscope with the decontamination fluid. Exemplary racks 100 sit inside the processing tray and are fed fluid through one central fluid supply connection (for example, fluid inlet 116). As such the fluid exiting from the nozzles may coat the surfaces shadowed by rack 100. The fluid may exit from the nozzles with sufficient pressure to lift some or all of the shadowed portions of the endoscope off of rack 100 such that, during fluid flow, these surfaces are not shadowed.

Rack 100 shown in FIG. 1 has four extension portions 120 extending from a central portion 110. Central portion 110 includes a circular ring 111. Central portion 110 can have a shape other than a circle. Rack 100 can have fewer or more extension portions 120. In FIG. 1, extension portions 120 extend radially from, and are arranged symmetrically around, central portion 110 such that each extension portion 120 is located 90 degrees from the adjacent extension portions 120. Extension portions 120 can be arranged asymmetrically around central portion 110. One or more of extension portions 120 can extend from central portion 110 at an angle other than radially from a center 118 of central portion 110. Central portion 110 includes a fluid inlet 116 that is, in this example, centrally located in central portion 110. Fluid inlet 116 is configured to connect to a fluid supply that is external to rack 100. Rack 100 can include more than one fluid inlet 116 and/or position fluid inlet 116 in some other location.

As shown in FIG. 1, central portion 110 has a perimeter wall 112 that surrounds center 118. Perimeter wall 112 has a plurality of openings 114 in lower regions of perimeter wall 112 that permit fluid to move between inside central portion 110 and outside central portion 110.

Figure 4:
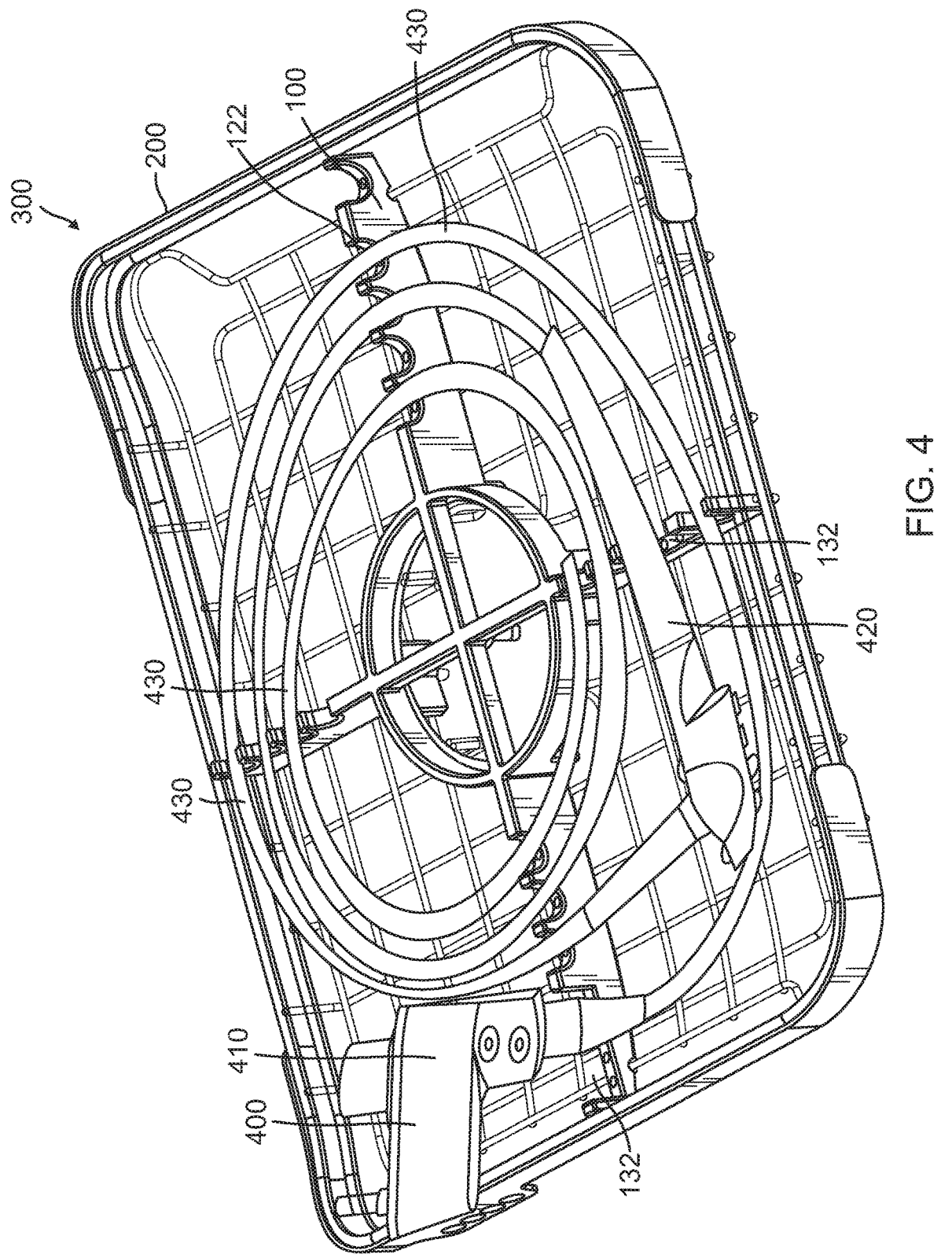
FIG. 4 depicts a perspective view of an endoscope in the decontamination system of FIG. 3.

In FIG. 1, rack 100 has a plurality of curved or semicircular receiving areas 122 formed in upper regions of extension portions 120. Receiving areas 122 are shaped to receive a tubular section of an endoscope or other instrument. Receiving areas 122 are arranged to facilitate the coiling of the tubular sections of the endoscope such that no part of the tubular sections contacts any other part of the tubular sections (as shown in FIG. 4). Rack 100 may also have other shaped receiving areas. As shown in FIG. 1, rack 100 has two receiving areas 132 that are rectangular in shape and are designed to receive parts of an endoscope other than the tubular section, i.e., control portions such as a light connector 410 and control body 420 (FIG. 4). Rack 100 can have receiving areas designed to support particular parts or sections of particular instruments.

FIG. 1 further shows ejection ports 124 located in a lower surface 123 of each receiving area 122. In FIG. 1, receiving areas 132 are shown with multiple ejection ports 124. During decontamination, decontamination fluid is introduced into fluid inlet 116, travels through passageways in extension portions 120 (shown in detail below), and is ejected from ejection ports 124. The decontamination fluid can be expelled from ejection ports 124 with sufficient force to lift the instrument so that the instrument no longer contacts receiving areas 122, 132 or other portions of rack 100. The instrument may be lifted only slightly, such as, for example, only enough to allow a layer of the decontamination fluid to completely separate the instrument from receiving areas 122, 132. In this manner, the decontamination fluid is provided to areas of the instrument that would not be contacted by the decontamination fluid in the absence of ejection ports 124. Put another way, the shadowing of these surfaces may be eliminated by this lifting action. The size and shape of the particular receiving area 122, 132 is based in part on the number of ejection ports provided that are provided in the particular receiving area 122, 132. For example, a larger receiving area 122, 132 may be provided with a larger number of ejection ports 124 to ensure that the lower surface of the portion of the instrument supported by that receiving area is completely covered by the decontamination fluid. For example, receiving area 132 can have two or more ejection ports 124, whereas receiving area 122 can include a singular ejection port 124. As seen in FIG. 4 the light connector and control body of receiving areas 132

Figure 2:
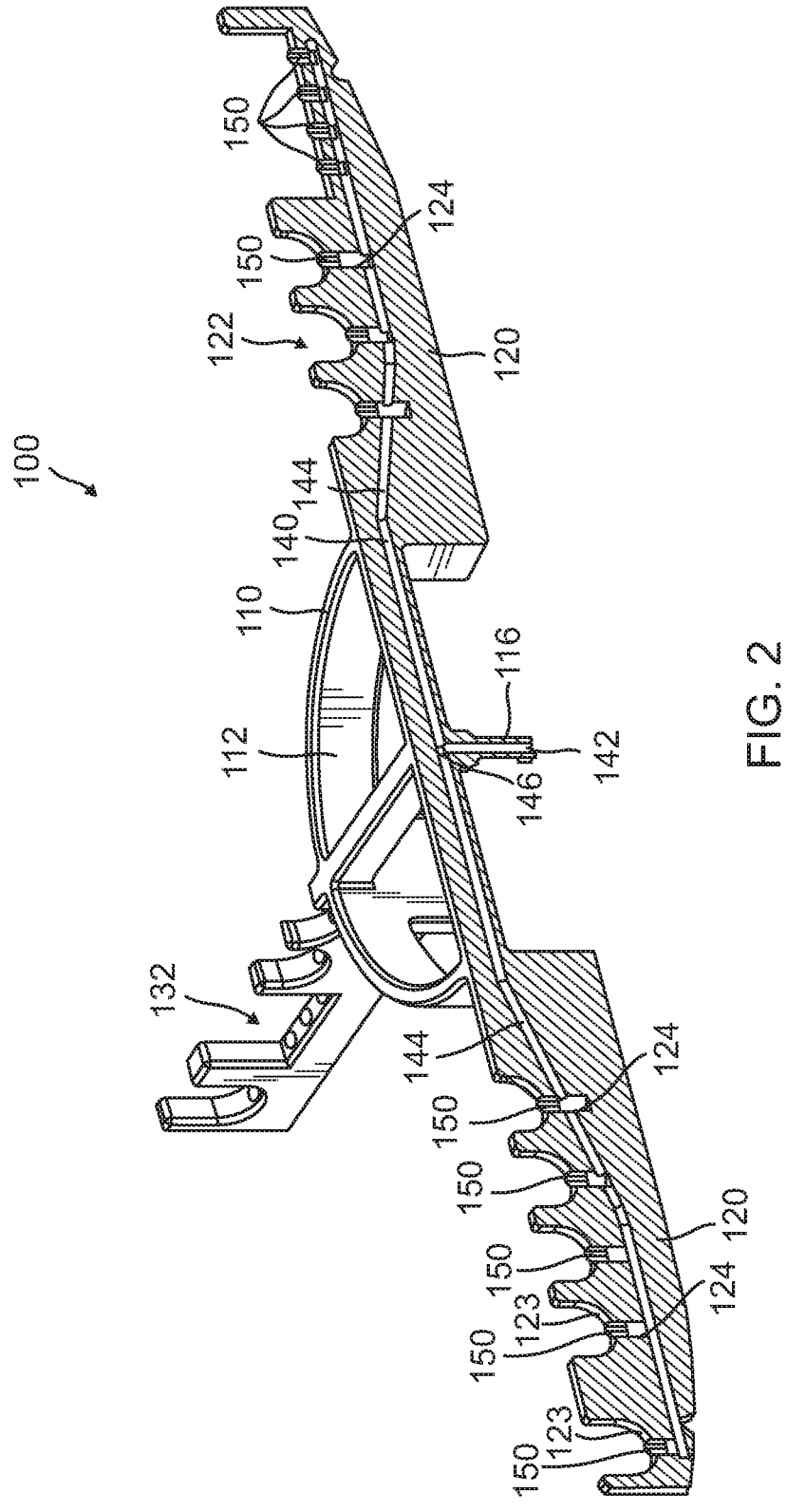
FIG. 2 depicts a sectional view along section line 2-2 of the decontamination rack of FIG. 1.
Figure 3:
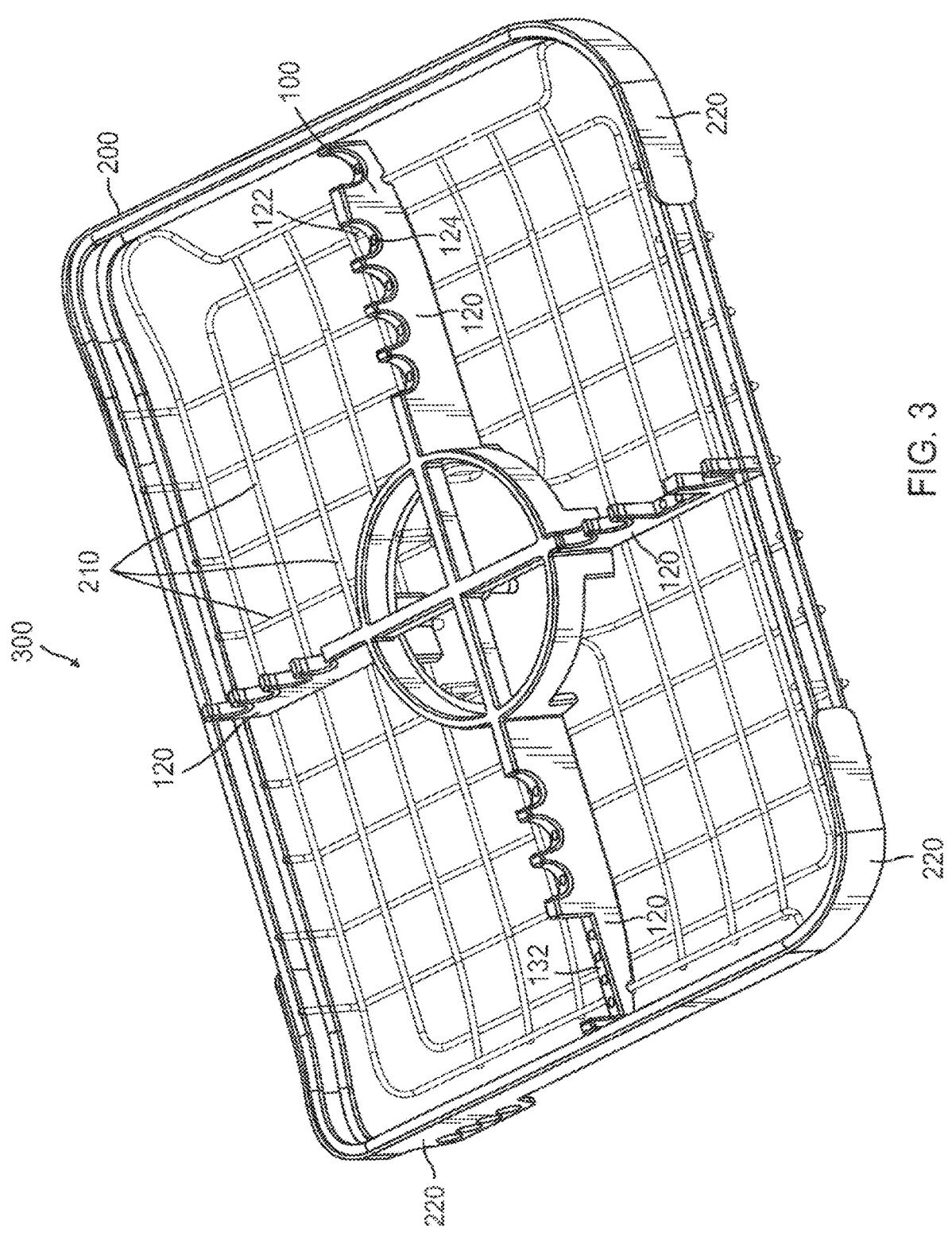
FIG. 3 depicts a perspective view of an exemplary decontamination system.

FIG. 2 is a sectional view along section line 2-2 in FIG. 1. FIG. 2 shows a fluid pathway 140 that connects an inlet opening 142 of fluid inlet 116 to ejection ports 124. In this example, fluid pathway 140 includes an intersection 146 where a plurality of sections 144 fluidly intersect. Each section 144 extends through one extension portion 120 to provide decontamination fluid to each ejection port 124 in that extension portion 120. In FIG. 2, section 144 is shown having the same cross-sectional area along the length of section 144. The cross-sectional area of section 144 can be different at different points along section 144. For example, the cross-sectional area of section 144 is smaller after every ejection port 124 (in a downstream direction) in order to balance the pressure of the decontamination fluid across the different ejection ports 124 of extension portion 120. The cross-sectional area of section 144 near intersection 146 in one extension portion 120 can be different from the cross-sectional area of section 144 near intersection 146 in a different extension portion 120 due to, for example, a different number of ejection ports 124 in the two extension portions 120. FIG. 2 shows one fluid inlet 116 supplying the decontamination fluid to all ejection ports 124. Two or more inlet ports can supply the decontamination fluid to ejection ports 124. For example, one fluid inlet can be provided for each extension portion 120.

FIG. 2 further shows a fluid nozzle 150 located in each ejection port 124. In FIG. 2, a particular fluid nozzle 150 has an aperture with a cross-sectional area that is smaller than the cross-sectional area of the ejection port 124 in which the particular fluid nozzle is located. In this manner, the pressure of the decontamination fluid is greater at the aperture of fluid nozzle 150 than it is in ejection port 124 immediately upstream of fluid nozzle 150. Different ones of fluid nozzles 150 can have apertures of different cross-sectional areas in order to, for example, balance pressure and/or flow volume of the decontamination fluid. Fluid nozzles 150 having different aperture cross-sectional areas can be used in conjunction with sections 144 that have different cross-sectional areas to provide a desired pressure and/or flow balancing.

In FIG. 2, fluid nozzle 150 is a flexible material such as, for example, silicone or rubber. In FIG. 2, fluid nozzle 150 is elastically deformable. In FIG. 2, one or more of fluid nozzles 150 extend vertically above a lower surface 123 of receiving area 122, 132. Fluid nozzle 150 can be a rigid material. A top surface of one or more of fluid nozzles 150 can be mounted flush with, or below, lower surface 123.

FIG. 3 shows a decontamination system 300 that includes decontamination rack 100 and a tray 200. Tray 200 has a plurality of wire members 210 that form a bottom structure of tray 200. Decontamination rack 100 is supported by wire members 210. A plurality of perimeter members 220 form a vertical region around a perimeter of tray 200. In FIG. 3, the bottom structure of tray 200 allows the decontamination fluid (or any other fluid) to drain away from decontamination rack 100. Tray 200 and decontamination rack 100 can be placed in a decontamination or reprocessing system that supplies the decontamination fluid to decontamination rack 100. Tray 200 can have a solid perimeter member 220 and/or a solid bottom structure. Although shown in a grid array in FIG. 3, wire members 210 can be in other configurations which support rack 100 while still allowing drainage.

FIG. 4 shows an endoscope 400 in position in decontamination rack 100. As shown in FIG. 4, tubular sections 430 of endoscope 400 are positioned in receiving areas 122 such that contact between portions of tubular sections 430 are minimized or eliminated, particularly when decontamination fluid exits ports 124 or nozzles 150. Control portions of endoscope 400, i.e., light connector 410 and control body 420, are positioned in receiving areas 132. The provision of the plurality of receiving areas 122, 132 allows the positioning of endoscope 400 shown in FIG. 4.

By virtue of the embodiments illustrated and described herein, Applicant has devised a method and variations thereof for decontaminating an instrument such as, for example, an endoscope.

In an exemplary method, an instrument is disposed in decontamination rack 100 of decontamination system 300 such that the instrument rests on at least one receiving area 122, and decontamination fluid is ejected through fluid ejection port 124 of receiving area 122 such that the decontamination fluid contacts and lifts the instrument. The decontamination fluid is ejected through fluid ejection port 124 of receiving area 122 with sufficient pressure to move the instrument away from a surface of receiving area 122.

Any of the examples or embodiments described herein may include various other features in addition to or in lieu of those described above. The teachings, expressions, embodiments, examples, etc., described herein should not be viewed in isolation relative to each other. Various suitable ways in which the teachings herein may be combined should be clear to those skilled in the art in view of the teachings herein.

Having shown and described exemplary embodiments of the subject matter contained herein, further adaptations of the methods and systems described herein may be accomplished by appropriate modifications without departing from the scope of the claims. In addition, where methods and steps described above indicate certain events occurring in certain order, it is intended that certain steps do not have to be performed in the order described but in any order as long as the steps allow the embodiments to function for their intended purposes. Therefore, to the extent there are variations of the invention, which are within the spirit of the disclosure or equivalent to the inventions found in the claims, it is the intent that this patent will cover those variations as well. Some such modifications should be apparent to those skilled in the art. For instance, the examples, embodiments, geometrics, materials, dimensions, ratios, steps, and the like discussed above are illustrative. Accordingly, the claims should not be limited to the specific details of structure and operation set forth in the written description and drawings.

I claim:

1. A decontamination rack, comprising:
a central portion comprising a fluid inlet;
an extension portion, extending from the central portion, including a first receiving area and a second receiving area, the first and second receiving areas having different numbers of fluid ejection ports as well as different shapes to receive different parts of a device to be decontaminated; and
a fluid pathway fluidly connecting the fluid inlet to the fluid ejection ports at the first and second receiving areas.

2. The decontamination rack of claim 1, in which a first number of fluid ejection ports are located in a lowermost area of the first receiving area, or at least one ejection port is located in a lowermost area of the second receiving area.

3. The decontamination rack of claim 1, in which second receiving area comprises a curved portion to receive a tubular section of the device to be decontaminated.

4. The decontamination rack of claim 1, further comprising a plurality of fluid nozzles located in each of the fluid ejection ports.

5. The decontamination rack of claim 4, in which a portion of each fluid nozzle of the plurality of fluid nozzles extends vertically above a surface of the first or second receiving area.

6. The decontamination rack of claim 4, in which the plurality of fluid nozzles are configured to expel decontamination fluid with sufficient force to lift at least a portion of the device from the first or second receiving area.

7. The decontamination rack of claim 1, further comprising: a plurality of extension portions, extending radially from the central portion.

8. The decontamination rack of claim 7, in which the plurality of extension portions are arranged symmetrically around the central portion.

9. The decontamination rack of claim 8, in which the fluid pathway comprises a plurality of pathway sections such that each of the plurality of pathway sections extends into one of the plurality of extension portions.

10. The decontamination rack of claim 9, in which the plurality of extension portions comprises a plurality of receiving areas arranged to facilitate coiling of tubular sections of the device.

11. The decontamination rack of claim 1, in which the first and second receiving areas are arranged along a longitudinal direction of the extension portion.

12. The decontamination rack of claim 1, in which the first and second receiving areas on the extension portion have a different distance from the central portion.

13. The decontamination rack of claim 1, in which the device is an endoscope, and the first receiving area has a shape suitable for supporting a control portion of the endoscope.

14. The decontamination rack of claim 4, in which a first fluid nozzle of the plurality of fluid nozzles includes a first aperture having a first cross-sectional area and a second fluid nozzle of the plurality of fluid nozzles includes a second aperture having a second cross-sectional area that is different than the first cross-sectional area.

15. A decontamination system, comprising:
a tray; and
the decontamination rack of claim 1 disposed in the tray, in which the fluid inlet is connected to a source of decontamination fluid.

16. The decontamination system of claim 15, in which the decontamination rack is configured to use the first receiving area to receive a control portion of an endoscope and use the second receiving area to receive a tubular portion of the endoscope.

17. A method of decontaminating an instrument, comprising:

receiving a non-tubular section of the instrument at a first receiving area of a decontamination rack;

receiving a tubular section of the instrument at a second receiving area of the decontamination rack; and ejecting decontamination fluid through respective fluid ejection ports of the first or second receiving areas such that the decontamination fluid contacts the instrument.

18. The method of claim 17, in which the ejecting comprises ejecting the decontamination fluid with sufficient pressure to lift at least a part of the instrument away from the first or second receiving area.

\*   \*   \*   \*   \*